United States Patent [19]

Borie et al.

[11] Patent Number: 5,020,297

[45] Date of Patent: Jun. 4, 1991

[54] APPARATUS FOR FILLING PETRI DISHES

[75] Inventors: Gérard Borie; Jean Pellegrin, both of Rennes; Alain Le Roch, Loudeac, all of France

[73] Assignee: Armor Equipment Scientifique, Combourg, France

[21] Appl. No.: 486,532

[22] Filed: Feb. 28, 1990

[30] Foreign Application Priority Data

Mar. 3, 1989 [FR] France ............................. 89 03008

[51] Int. Cl.⁵ ..................... B65B 3/12; B65B 43/40; B65B 55/08; B65B 63/08
[52] U.S. Cl. ........................................ 53/127; 53/167; 53/253; 53/281; 141/82; 141/130; 53/381.4
[58] Field of Search ................ 53/127, 168, 250, 281, 53/309, 381 A, 468, 900, 50, 167, 253; 141/82, 130

[56] References Cited

U.S. PATENT DOCUMENTS

| 2,902,804 | 9/1959 | Meulemans et al. ................. 53/127 |
| 2,987,163 | 6/1961 | Eddison et al. . | |
| 3,050,915 | 8/1962 | Silverstobe ...................... 53/381 A |
| 3,522,631 | 8/1970 | Niclas ................................... 53/127 |
| 3,531,621 | 5/1970 | Chamberlin .......................... 53/468 |
| 3,704,568 | 12/1972 | Duhring et al. ............. 53/381 A X |
| 3,719,023 | 3/1973 | Richardson ...................... 53/381 A |
| 4,170,861 | 10/1979 | Snyder et al. .............. 53/381 A X |
| 4,468,914 | 9/1984 | Pestes ............................ 53/381 A X |

FOREIGN PATENT DOCUMENTS 2018288 10/1979 United Kingdom .

Primary Examiner—John Sipos
Assistant Examiner—Linda B. Johnson

[57] ABSTRACT

The apparatus is fitted with a transfer turntable (1) suitable for conveying dishes in the open state from a station for dispensing open dishes to a filling station, and then from the filling station to a station for receiving filled dishes. The turntable comprises a top plate (10) whose openings retain the lids of the dishes and a bottom plate (11) whose openings receive the bottoms of the dishes, said bottoms resting constantly against a fixed refrigerated sole plate (55) while they are being transferred. The turntable (1) is driven by means of a drive disk (6) placed beneath the sole plate (55) and magnetically coupled to the turntable by means of two series of facing magnets (61-12). The apparatus is suitable for constituting laboratory equipment.

13 Claims, 5 Drawing Sheets

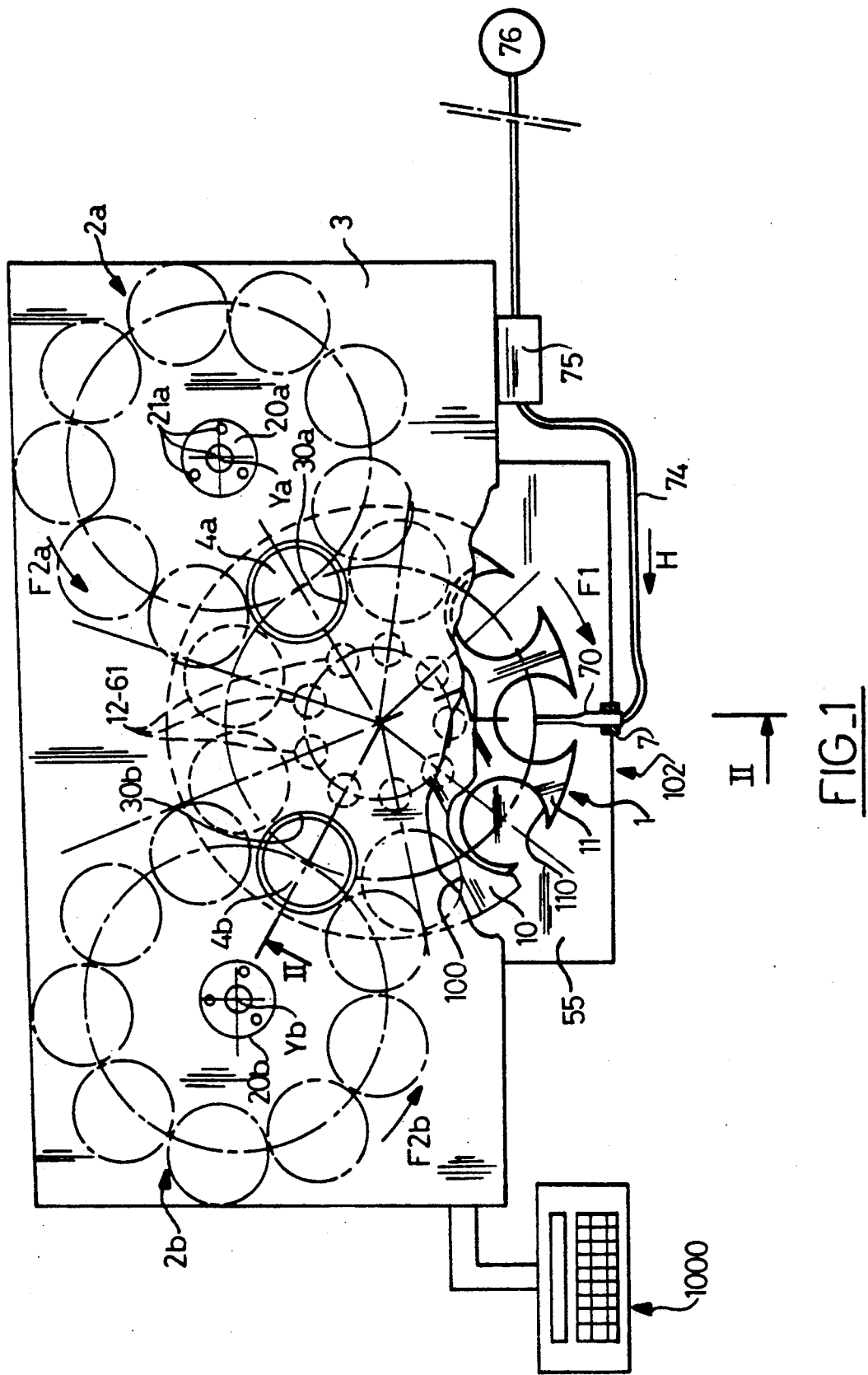
FIG_1

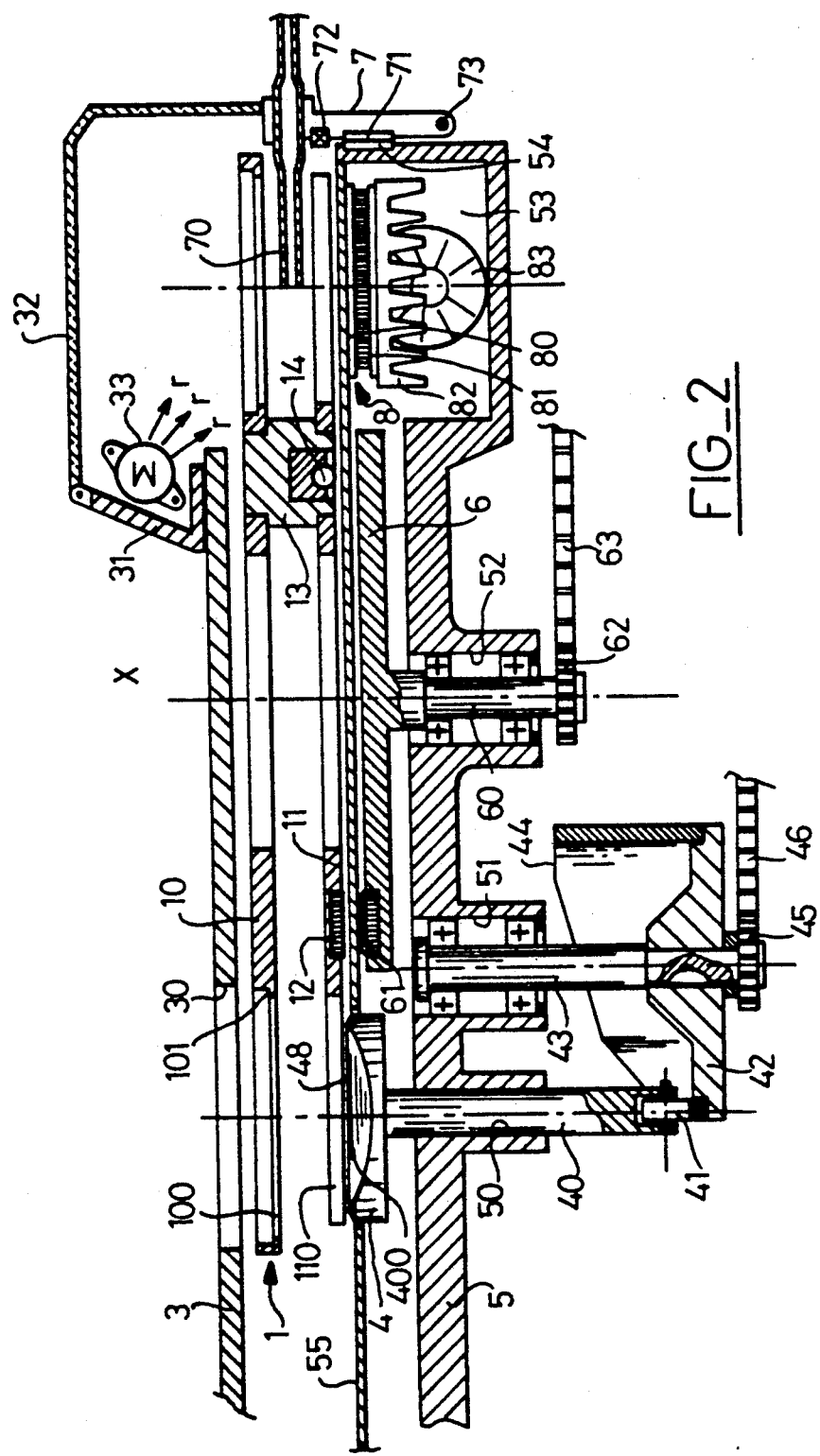
FIG_2

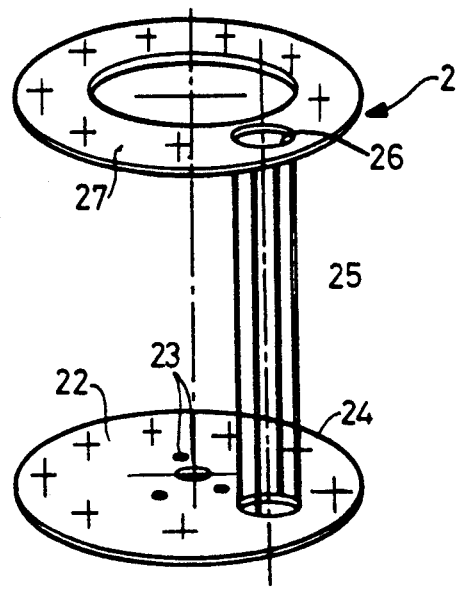
FIG_3
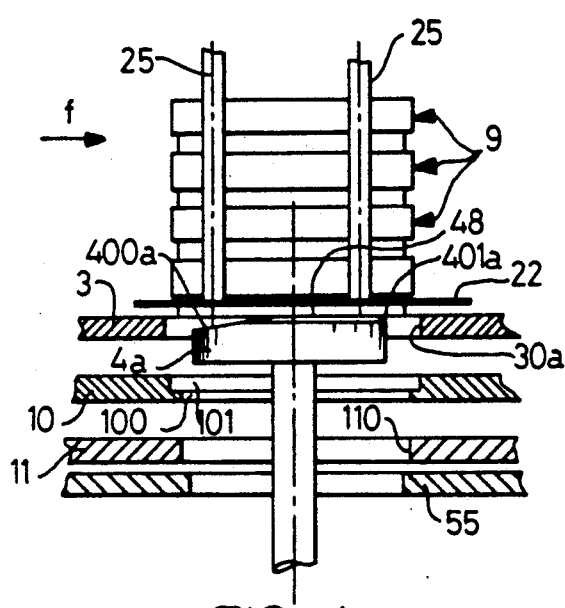
FIG_4
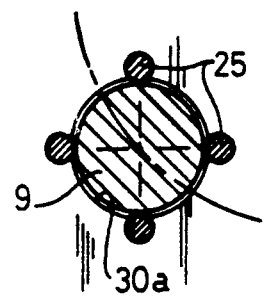
FIG_4a
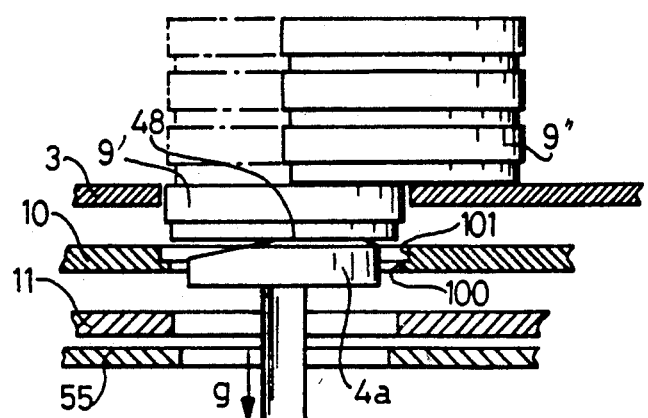
FIG_5
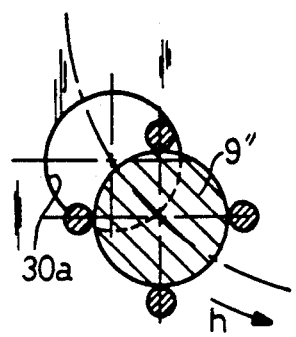
FIG_5a

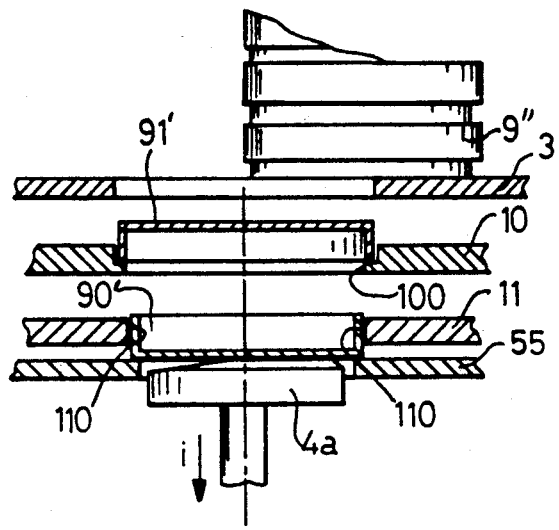
FIG_6
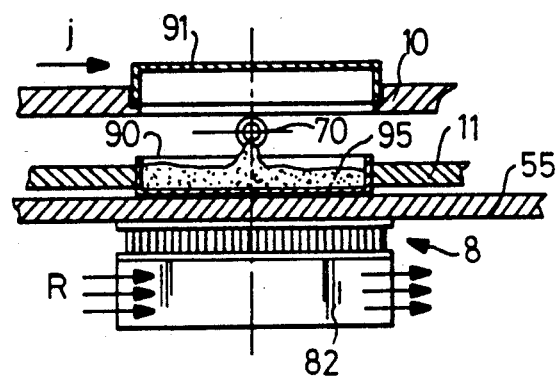
FIG_7
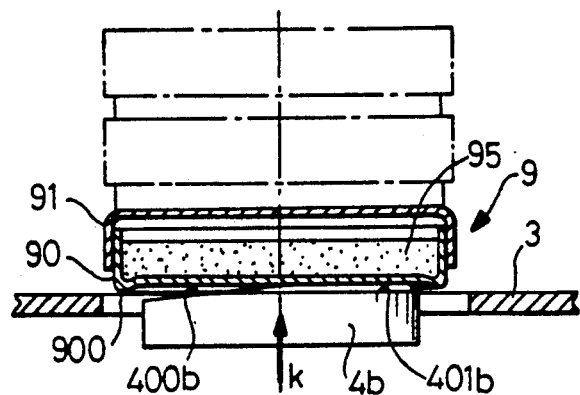
FIG_8
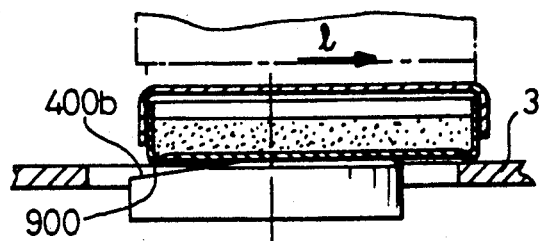
FIG_9

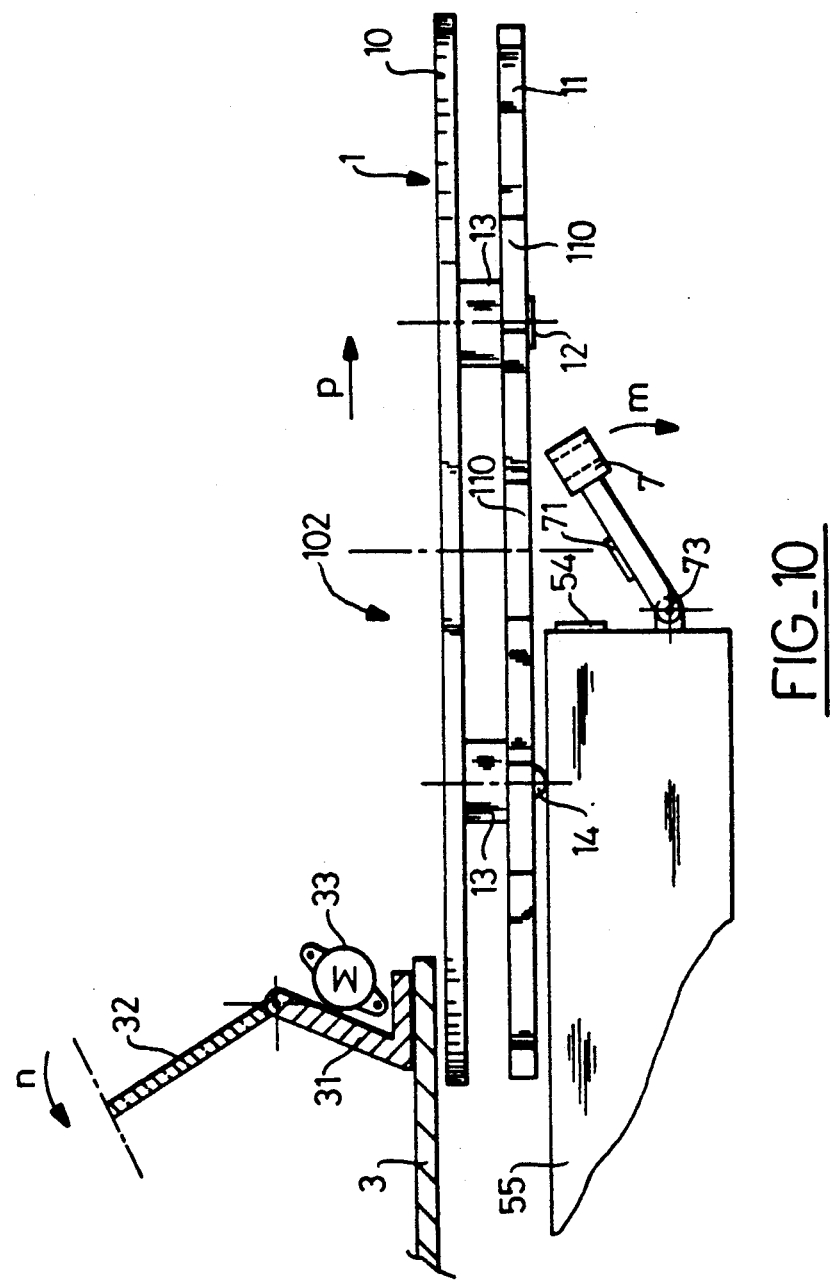
FIG_10

APPARATUS FOR FILLING PETRI DISHES

The present invention relates to apparatus for filling petri dishes. Petri dishes are small circular boxes made of transparent plastic material and containing a nutrient such as a mixture of gelose and distilled water. They are used as a development medium for cultures containing microorganisms and they are used in large numbers in analysis laboratories, in particular in medical research and in industry.

At ordinary temperature, the mixture of gelose and distilled water is in the form of a solid having the consistency of gelatin. Before being inserted in petri dishes at a temperature of about 45° C. to 50° C., the mixture is raised to a temperature of about 100° C. in order to take up the liquid form. It is thus spread in the dishes to form a regular layer with a plane surface. A dish cannot be used until after the substance has hardened, with the hardening time being about 10 minutes at ambient temperature.

Proposals have already been made for apparatuses intended to fill dishes automatically.

Thus, the document FR-A-2 433 752 describes filling apparatus in which the dishes to be filled are conveyed one after another by means of a horizontal turntable to a filling station which includes a gelose dispensing nozzle. The dishes are presented to the gelose dispensing station one after the other and in the open state, i.e. with their lids held up above their bottoms. This is made possible by virtue of the transfer turntable comprising two superposed and coaxial circular horizontal plates, each of which is pierced by circular openings regularly distributed around its periphery and in register with the openings in the other. The openings in the top plate are slightly smaller in diameter than the lids but slightly greater in diameter than the bottoms of the dishes, thereby allowing the dishes to pass through them while retaining the lids only. In contrast, the bottom plate is provided with openings that are shaped to receive and support the bottoms of the dishes while transferring them.

The gelose dispensing nozzle extends between the two plates, thereby enabling it to apply gelose to the bottoms of the dishes as they are presented one after the other to the filling station.

This prior apparatus is fitted with a single carousel which serves both as a dispensing station for empty dishes and as a receiving station for full dishes. The carousel contains several piles of dishes which are distributed around its periphery in the form of columns, said columns being held by vertical rods.

Although this prior apparatus generally gives satisfaction, it nevertheless suffers from certain drawbacks.

Firstly, its dish-containing capacity and consequently the amount of work it can perform unattended are limited by the fact that a single carousel is used. Increasing the number of columns per carousel would give rise to problems related to weight and size.

Secondly, the system for transferring the dishes from the carousel to the transfer table, and back from the table to the carousel (after filling) is relatively complicated and subject to breakdowns since it is necessary to make use of moving means which serve to retain the last dish but one in a column whenever the last or bottommost dish is taken or inserted. The complexity of this system also requires work to take place at a relatively slow rate.

Thirdly, as happens relatively often, faults arise in the filling process and these faults can lead to substance splashing or spilling beside the dishes, thereby giving rise to problems related to difficulties in cleaning the apparatus. Cleaning requires a large amount of disassembly, in particular it requires the turntable to be disassembled, and it therefore immobilizes the apparatus for a relatively long period of time, during which time production is stopped.

Fourthly, full dishes are stacked while the substance is still liquid and this can give rise to defects in the surface planeness of the gelose in the dishes by virtue of the inevitable shaking of the substance that occurs during storage. Defects in planeness run the risk of giving rise to difficulties, in particular during subsequent analyzes based on reading by means of a camera.

Finally, it is not possible to take off a column of full dishes that have just been stored in the carousel for immediate utilization because of the time required for the substance to cool, as mentioned above. This may be a drawback when operating personnel find themselves short of petri dishes and faced with an urgent requirement.

The invention seeks to solve these various problems by proposing apparatus of the type mentioned above which is simple in design, safe and reliable in operation, which operates at a high rate, which is easy to maintain, in particular for cleaning purposes, which has a large storage capacity, i.e. which is capable of containing and processing a very large number of dishes without external intervention, which enables genuinely plane-surfaced layers of gelose to be obtained, and which produces petri dishes ready for immediate use (without a waiting period). According to the invention, these various results are achieved by virtue of the fact that the apparatus (like the prior art apparatus mentioned above) comprises a transfer turntable suitable for conveying open dishes (having their lids held up above their bottoms) to be conveyed successively and step-by-step from an empty dish dispensing station to a filling station, and then from the filling station to a full dish receiving station, said turntable comprising two superposed coaxial circular horizontal plates each pierced by a series of circular openings regularly distributed around its periphery and in register with the openings of the other plate, the diameter of the openings in the top plate being slightly smaller than the diameter of the lids and slightly larger than the diameter of the bottoms, thereby enabling the bottoms to pass therethrough while retaining only the lids, and is characterized in that:

firstly, the openings in the bottom plate are slightly larger in diameter than the bottoms so that they too allow the bottoms to pass therethrough; and secondly, the said transfer turntable rests via its bottom plate on a fixed sole plate which is plane and horizontal, such that the dish bottoms rest on said sole plate while they are being transferred by means of said bottom plate, the turntable being rotated by drive means situated beneath the sole plate and acting via magnetic coupling.

In addition, according to other advantageous characteristics of the invention:

the said sole plate is refrigerated, e.g. by means of Peltier effect cooling modules;

the said dish-distributing and receiving stations comprise distinct storage means constituted by identical carousels in which the dishes are stacked in columns, stepwise rotation of the carousels taking place synchronously with rotation of the said transfer turntable in such a manner that the empty dishes leave the dispensing carousel one by one by escaping in succession from the bottoms of adjacent columns, while filled dishes are inserted one by one into the receiving carousel via the bases of adjacent columns;

the columns of dishes contained in said carousels rest on a horizontal slab overlying said transfer turntable, said slab being pierced at each of the distributing and receiving stations by respective openings allowing dishes to pass from the dispensing carousel to the turntable and from the turntable to the receiving carousel;

the means for rotating the said carousels impart two successive half-strokes to each carousel for each dish, each half-stroke corresponding to one half of the angular spacing between two adjacent columns;

two transfer pistons are provided, one situated at the dispensing station and the other at the receiving station, the pistons being slightly smaller in diameter than the dishes, and means such as rotary cams are provided for displacing the pistons vertically on the axis of the associated openings;

the said means serve to bring each piston into each of the following positions in succession:

(a) a high position in which the top face of the piston lies substantially flush with said horizontal slab;

(b) an intermediate position in which the top face lies below the lever of the horizontal slab by an amount corresponding substantially to the height of one dish; and (c) a low position in which the top face lies substantially flush with said sole plate;

the top face of each piston has a sloping flat and/or a chamfer;

the transfer turntable is driven by means of a horizontal drive disk disposed immediately beneath the sole plate vertically below the turntable, said drive disk and the bottom plate each being provided with a series of magnets regularly distributed around their respective peripheries and facing one another;

the said bottom plate bears against the sole plate via antifriction means such as balls and/or ball bearings;

said filling station comprises a nozzle for injecting a substance such as gelose, which nozzle is fed by a pump and is normally positioned horizontally between the two plates of the transfer turntable, with the nozzle being carried by a lever capable of being retracted by being tilted so as to disengage the access to the sole plate, thereby enabling said turntable to be removed;

said bottom plate is notched to the outside at each of its openings, thereby enabling the presence of a dish bottom in each opening to be detected by means of an opto-electronic detector situated at the filling station; and it is provided with a germicidal device comprising an ultraviolet radiating tube to which the dishes are exposed as they pass to the filling station.

Other characteristics and advantages of the invention appear from the description and the accompanying drawings which show a preferred embodiment.

In the drawings:

FIG. 1 is a partially cutaway diagrammatic plan view of the apparatus;

FIG. 2 is a section on staggered vertical plane II—II through the apparatus of FIG. 1 and drawn to a larger scale;

FIG. 3 is a diagrammatic and incomplete perspective view of a dish storage carousel;

FIGS. 4, 5, 6, and 7 are diagrammatic vertical section views showing various stages in taking and transferring empty dishes to the filling station;

FIGS. 4a and 5a are diagrammatic plan views corresponding respectively to the situations shown in FIGS. 4 and 5, and drawn on a smaller scale;

FIGS. 8 and 9 are diagrammatic vertical section views showing how a full dish is stored at the receiving station; and FIG. 10 is a diagrammatic side view of the machine for showing how the transfer turntable is removed, in particular to enable the apparatus to be cleaned.

The apparatus shown diagrammatically in plan view in FIG. 1 is generally in the form of a rectangular box covered by a stainless steel slab 3. Various items of equipment for controlling the apparatus are installed inside the box, in particular motors for driving the moving parts and electronic components constituting the microprocessor controlling the machine. The microprocessor is connected to a keyboard 1000 which serves in conventional manner to enable the operator to respond to requests from the microprocessor for instructions and to give the microprocessor information as a function of the desired operation. This information relates in particular to the number of dishes to be processed and to the volume of gelose that is to be dispensed into each dish.

Reference 102 designates that face of the apparatus which is directed towards the operator (i.e. downwardly directed in FIG. 1). In the central portion of the apparatus, close to said front face, there is a turntable 1. Towards the back of the apparatus disposed symmetrically on either side of the turntable 1, there is one station for dispensing empty dishes and another for receiving full dishes. The component parts of these two stations are identical and consequently they have the same references, with the index (a) being given to items in the dispensing station (to the right in FIG. 1) and the index (b) being given to items in the receiving station (to the left in the figure).

The station for filling the dishes with a nutrient substance, such as a mixture of gelose and distilled water, is situated in the middle of the front face of the apparatus and comprises a dispensing nozzle or hollow needle 70 which is connected by a flexible hose 74 to a source 76, in this case a receptacle containing gelose in the liquid state. An appropriate pump 75, preferably of the peristaltic type, is adapted to pumping successive volumes of gelose from the source 76 without jerking (in order to avoid generating bubbles) which volumes are then injected into the dishes by the nozzle 70. Arrow H symbolizes the flow of gelose along the hose 74. The pump 75 may have one or two paths and is adapted to deliver a variable volume that preferably lies in the range 3 ml to 25 ml. The filling rate is advantageously about 10 dishes per minute at 15 ml of substance.

In each of its dish dispensing and receiving stations, the apparatus includes a rotary disk 20 for driving a carousel containing the dishes. The disk is mounted to rotate about a vertical axis Y and it is driven by an appropriate electric motor housed beneath the slab 3 inside the box constituting the body of the apparatus. The disks 20 have studs 21 for centering and driving the carousels. As can be seen in FIG. 3, each carousel comprises a bottom horizontal disk 22 and a top ring 27. The disk 22 has orifices 23 suitable for being put into place on the disk 20 and co-operating with its centering and drive studs 21. This disk 22 has a series of peripheral openings 24 which are uniformly distributed angularly. The diameter of the openings 24 is slightly greater than the diameter of the dishes. FIG. 3 shows only one opening 24, but nine such openings 24 are provided at 40° intervals relative to one another. Corresponding openings 26 are provided in the top ring 27 and the parts 22 and 27 are connected to each other by means of a series of vertical rods 25. Four rods 25 are provided per pair of openings 24, 26 said rods serving to retain a stack of dishes constituting a vertical column received between the rods. Each column advantageously holds 50 petri dishes, so that the carousel may contain a total of 450 dishes. For each set of four rods 25 provided per column, at least one of these rods situated on the outside of the carousel is flexible and its top end is movable, thereby facilitating removing a column of dishes or some of the dishes constituting the column.

After being put into place on the disks 20a and 20b, the carousels are driven step-by-step by said disks in a direction which is anticlockwise when seen from above, which direction is represented by arrows F2a and F2b in FIG. 1.

The transfer turntable 1 is constituted by two circular plates 10 and 11 which are fixed to each other by means of a series of spacers 13. They are advantageously made of a strong plastic material. The top plate 10 is pierced by a series of nine openings disposed around its periphery and regularly distributed at 40° intervals. Each of these openings 100 has an upwardly directed portion 101 of slightly larger diameter. The bottom plate 11 is slightly smaller in diameter than the plate 10 and similarly has nine peripheral openings 110 at 40° intervals having vertical axes coinciding with those of the openings 100. Because of the smaller diameter of the plate 11, its openings 110 have notches opening to the outside.

Traditionally petri dishes are small boxes of transparent plastic material comprising two portions: a bottom and a lid. These portions have side walls of different diameters, with the wall of the lid overlying the wall of the bottom when the dish is closed. This engagement takes place practically without friction so the lid can be removed without effort.

According to an important characteristic of the invention, the diameter of the circular openings 100 in the top plate is smaller than the diameter of a lid such that lids are retained by the rim of the larger diameter portion 101 if the dish is moved up and down along the axis of the opening. However, the diameter of the openings 100 is slightly larger than the diameter of the bottom of a dish, thereby enabling the bottom to continue downwards through an opening 100, thus escaping from its lid. The diameter of the circular openings 110 is likewise very slightly larger than the diameter of the bottom of a dish.

A series of magnets 12 is received in the bottom face of the plate 11, there being, for example, nine such magnets regularly distributed at 40° intervals. The turntable 1 rests on a series of balls 14, e.g. three balls disposed at 120° intervals, which balls are advantageously received in the spacers 13 on a fixed horizontal slab 55 referred to as a "sole plate". The balls may advantageously be replaced by ball bearings. The slab 55 is made of non-magnetic material, preferably an aluminum alloy. Reference 5 designates a solid slab constituting the frame of the apparatus. It extends a short distance beneath the sole plate 55 and includes a plurality of vertical axis guide bearings 50, 51, and 52 whose function is explained below.

The bearing 52 serves to guide rotation of a shaft 60 about a vertical axis X by means of appropriate ball bearings. The shaft is fixed to a disk 6 likewise made of non-magnetic material such as an aluminum alloy and disposed horizontally immediately beneath the sole plate 55. The disk carries a series of magnets 61 identical to the magnets 12 and disposed in register therewith. The shaft 60 is rotated by an appropriate motor (not shown) e.g. by means of a cog belt 63 meshing with a sprocket 62 fixed to the shaft 60. If the turntable 1 is put into place on the sole plate 55 in such a manner as to cause the axis of the turntable to be close to the axis X, then under the mutual magnetic attraction of the magnets 61 and 12, the turntable will take up a position where it is exactly in alignment with the disk so that the magnets 12 and 61 face one another exactly, after which the turntable 1 is driven by rotating the disk 6 and by magnetic coupling.

At each of the dispensing and receiving stations, the top slab 3 is pierced with an opening 30a or 30b facing the trajectory of the corresponding carousel 2a or 2b, with the diameter of the opening being slightly greater than the diameter of the dishes. As the turntable 1 rotates, after being positioned on the axis X, each pair of openings 100, 110 may come into register with each of these two openings 30a and 30b.

Two pistons 4a and 4b are guided to move in translation along a vertical axis in alignment with respective ones of the openings 30a and 30b by respective bearings 50 formed on the frame slab 5. The piston 4b of the receiving station is shown in FIG. 2. An identical piston is situated in the dispensing station.

Each of the pistons 4 has a top face 48 with a chamfer edge 401 having a sloping surface 400 which, as explained below, facilitates passing the bottom of the dishes over the face 48.

The head of the piston 4 is carried by a rod 40 whose bottom end is provided with a cam-follower wheel 41 resting on the running path of an annular cam 44. The cam path is fixed on a disk 42 which is fixed on a vertical shaft 43 guided to rotate by ball bearings received in the bore 51. An appropriate electric motor and stepdown gear box (not shown) rotates the cam 42 by means of a cog belt 48 which meshes with a sprocket wheel 45 fixed to the shaft 43. Rotation of the cam 42 causes the piston to be moved vertically. As explained below, the cam profile is designed so as to give the piston three steady determined positiones: a low position; a high position; and an intermediate position.

Adjacent to the front face of the apparatus, the frame slab 5 has a hollow forming a box 53 which extends beneath a portion of the trajectory followed by the dishes while they are being transported by the turntable 1. This box 53 is fitted with a refrigerator 8. The refrigerator comprises a Peltier effect cooling module 8 appropriately powered with electricity by means not shown in the figures. A Peltier effect cell acts like a heat pump but without moving parts. It has a cold face where heat is absorbed by electrons passing from one semiconductor to another. The electricity supply provides the energy required to cause these electrons to pass through the system. The hot face releases energy to ambient air through a heat exchanger. The cold face 80 of the module 8 is glued directly to the underside of the sole plate 55 whereas the downwardly directed hot face 81 carries fins 82 for dissipating heat. A ventilation system including one or more fans 83 blows a flow of air at ambient temperature through the box 53 in order to remove the heat dissipated by the fins 82. The module 8 thus constantly cools the sole plate 55.

A plurality of modules 8 may be provided, advantageously connected in series and dispose d on the arc of a circle so as to cover at least a portion of the trajectory followed by the dishes while they are being conveyed through the apparatus by means of the turntable 1. The gelose dispensing nozzle 70 is disposed horizontally and extends between the two plates 10 and 11 so that its outlet orifice coincides substantially with the center of the openings 100 and 110. The nozzle 70 is removably received in a groove provided at the top end of a lever 7 which is hinged to the frame of the apparatus about a horizontal axis 73. The lever 7 is normally maintained in a vertical position by means of a magnet 54 carried by a frame and co-operating with another magnet 71 on the lever. The lever is thus easily tilted forwards by pivoting about the axis 73, thereby disengaging the front face of the apparatus, in particular for removing the turntable 1 for cleaning purposes, as described below.

A protective cap 32, preferably made of transparent plastic, is disposed above the filling station containing the nozzle 70, and is hinged to a support 31 fixed to the top slab 3. A germicide constituted by a lamp 33 emitting ultraviolet radiation is disposed beneath the cap 32. This radiation represented by arrows r is directed towards the dishes passing through the gelose feed station and is intended to destroy germs, microbes, and other microorganisms the may be found in the dishes, thereby ensuring that the gelose-filled dishes are produced in a properly sterile condition.

It may also be observed that the filling station is provided with a detector represented diagrammatically in FIG. 2 at reference 72. This is a conventional type of detector, e.g. an opto-electronic detector having cells for emitting and receiving electromagnetic radiation, and directed towards the notches corresponding to the openings 110 in the bottom plate. If a petri dish bottom is not in the opening, then the radiation is not reflected. Thereby indicating that there is no dish bottom, and a signal indicative of this anomaly is then delivered to the microprocessor.

The apparatus is used as follows:

A carousel containing the quantity of petri dishes to be filled is installed on the dish dispensing station, with the bottom disk 22 of the carousel being placed on the drive disk 20a. The dishes to be processed are regularly disposed in each of the columns delimited by the vertical rods 25 so that all of the columns contain the same number of dishes, plus or minus 1 if the total is not divisible by 9. Another carousel containing no dishes is installed on the receiving station.

The operator uses the keyboard 1000 to instruct the microprocessor about the operation to be performed, and in particular specifies the number of dishes to be processed and the volume of gelose to be dispensed into each dish. At the beginning of operation, the drive disk 6 is rotated for a short period of time in order to ensure that the transfer turntable 1 is accurately centered on the axis X in case initial automatic centering has not been done adequately, and also in order to take up any small amount of backlash that may be present. The cams 44 are in a position such that the piston 4a is in its high position, i.e. its top face 48 is level with the top face of the slab 3. Conversely, the piston 4b is in its low position such that its top face 48 is flush with the sole plate 55 (the position shown in FIG. 2).

Appropriate detectors are provided for monitoring that the carousels and the transfer turntable are properly positioned at the beginning and throughout the operation.

The transfer of an empty dish and its delivery to the feed station are now described with reference to FIGS. 4 to 7. The carousel 2a is rotated so as to bring one of its dish dispensing openings 24 over the opening 30a. The piston 4a is in its high position (FIG. 4). The arrival movement of the column of empty dishes is shown in FIG. 4 by arrow f. The sloping surface 400a facilitates the bottom face of the dish sliding progressively from the slab 3 onto the piston 4a. The cam 42a is then rotated in order to lower the piston 4a to an intermediate position in which the face 48 is lowered through the height of one dish. This limited stroke downwards movement is represented in FIG. 5 by arrow g. The bottom dish in the stack, referenced 9' is thus extracted from the carousel. Thereafter, the carousel 2a is rotated through 20° so that the bottom dish 9'' in the stack of remaining dishes lies partly on the slab 3 and partly over the opening 30a (see FIG. 5a where this rotation of the carousel is represented by arrow h).

Continuing rotation of the cam 42 then lowers the piston 4a fully until it reaches a low position where its top face 48 lies in the same plane as the top face of the sole plate 55. During this downwards movement represented in FIG. 6 by arrow i, the lid 91' of the dish 9' is retained by the top plate 10 while the bottom of the dish 90' is received in the opening 110 in the bottom plate 11. The drive disk 6 is then rotated through 40° in order to bring the dish 9' in its open position to the filling station. This rotation is represented in FIG. 1 by arrow $F_l$. It takes place clockwise, i.e. in the opposite direction to carousel rotation. Another pair of openings 100, 110 is thus positioned beneath the opening 30a and the operation can begin again in order to extract the bottom dish from the stack corresponding to the next column in the carousel 2a. For this purpose, the carousel is rotated through another 20° in the same direction as before.

The dishes taken from the stacks thus arrive successively in the filling station with this movement being represented in FIG. 7 by arrow j.

During this displacement, and according to an important characteristic of the invention, the bottoms of the dishes 90 rest on the sole plate 55, i.e. on a refrigerated plane. This refrigeration of the dishes both before and after filling facilitates gelose cooling and thus accelerates hardening thereof.

When a dish to be filled reaches the nozzle 70. The microprocessor switches on the pump 75 which delivers a determined dose of gelose 95 to the nozzle from which it is injected into the dish bottom 90.

After filling and while still conveyed by the turntable 1, the dishes arrive in succession in the open state above the piston 4b which is then in its low position with its face 48 flush with the sole plate 55. At this stage, by virtue of the refrigeration function of the sole plate 55, the gelose has already practically solidified. The cam 42b then causes the full dish to be stored inside the receiving carousel 2b by operating in a manner similar to that used for extracting empty dishes, but in the reverse order. To do this, the rotary cam 42 initially raises the piston 4b to an intermediate level corresponding to being set back by half of a dish height beneath the slab 3. As it moves up, the piston 4 brings the bottom 90 into the lid 91 and consequently automatically closes the dish. With the piston in its intermediate position, the receiving carousel 2b is rotated so as to bring a column of full dishes to stand on the waiting dish. The piston 4b is then raised fully and is inserted into the bottom of the stack of dishes by raising it together with all the other dishes. The carousel 2b is then rotated through 20° so as bring the stack partially over the opening 30b and over the support surface constituted by the slab 3, waiting for the next dish.

It should be observed that the bottoms of the dishes are often somewhat concave, being delimited by a projecting rim 900. As the column of full dishes is passing from the piston onto the slab 3, the sloping surface 400b prevents this rim 900 catching on the piston (see FIG. 9) which would cause the dish to tilt and would run the risk of it jamming against the edge of the opening 30b.

In FIGS. 8 and 9, the piston raising motion and the displacement of the column of full dishes are represented respectively by arrows k and l.

In FIG. 7, arrows R represent the flow of air cooling the fins of the Peltier effect cooling system 8.

FIG. 10 shows how easy it is to remove the turntable, in particular for cleaning both the turntable and the support sole plate 55 in the event of gelose being accidently spilt inside the apparatus. To do this, the cap 32 is initially raised (arrow n). With the nozzle 70 removed, the lever 7 is tilted down (arrow m), thereby disengaging the front face 102 of the apparatus. Then by exerting sufficient forwardly directed horizontal force p on the turntable 1 to overcome the magnetic coupling attraction 61-12, the turntable 1 is moved and extracted. As it moves, the balls 14 roll over the sole plate 55 further facilitating the operation. After cleaning, it suffices to perform the same actions in the opposite direction and the turntable automatically takes up the proper position.

The microprocessor is programmed so that when the detector 72 detects there is no dish bottom in place, then the pump 75 is not switched on. This happens, in particular, when a dish is placed upsidedown in the carousel 2a, since the entire dish is then held up by the top plate 10. Since the pump is not switched on, there is no unwanted dispensing of gelose, and operation may continue normally without interruption for the other dishes. The upsidedown dish is stored normally, still upsidedown, together with full dishes in the receiving carousel 4b.

By way of numerical example, the speeds of advance are selected so as to obtain a throughput of about one dish every 6 seconds. The Peltier effect modules are designed so that at ambient temperature they reduce the temperature of the refrigerated slab to a value of about 7° C. to about 10° C. Under these conditions, gelose is almost hard when a filled dish arrives over the piston 4b, such that the movements of the dish during its storage have no or practically no effect on the planeness of the gelose surface.

The frame of the apparatus may be provided with a spirit level enabling the sole plate 55 to be set up exactly horizontal, thereby guaranteeing that the layer of substance is uniform in thickness.

Since the stored dishes are already cooled, it is possible to use them immediately.

We claim:

1. Apparatus for filling petri dishes, said dishes being circular in shape, comprising a bottom onto which a lid of slightly larger diameter than the bottom is fitted freely, the apparatus being of the type comprising a transfer turntable (1) suitable for conveying open dishes (9) having their lids (91) held up at a distance above their bottoms (90) in succession and step by step from an empty dish dispensing station to a dish-filling station, and then from the dish-filling station to a filled dish receiving station. Said turntable (1) comprising two superposed coaxial circular horizontal plates (10, 11) each pierced by a series of circular openings regularly distributed around its periphery and in register with the openings in the other disk, the diameter of the openings (100) in the top disk (10) being slightly smaller than the diameter of the lids (91) but slightly larger than the diameter of the bottoms (90), thereby allowing the bottoms to pass therethrough while retaining the lids, the apparatus being characterized in that:

firstly the openings (110) in the bottom plate (11) are slightly larger in diameter than the bottoms (90) so that they too allow the bottoms to pass therethrough; and secondly the said transfer turntable (1) rests via its bottom plate (11) on a fixed sole plate (55) which is plane and horizontal, such that the dish bottoms (90) rest on said sole plate (55) while they are being transferred by means of said bottom plate (11), the turntable (1) being rotated by drive means (63, 62, 6) situated beneath the sole plate (55) and acting via magnetic coupling (61, 12).

2. Apparatus according to claim 1, characterized in that said sole plate is refrigerated.

3. Apparatus according to claim 1, characterized in that the said empty dish dispensing, said dish filling and said filled dish receiving stations comprise distinct storage means constituted by identical carousels (2a, 2b) in which the dishes (9) are stacked in columns, stepwise rotation of the carousels taking place synchronously with rotation of the said transfer turntable (1) in such a manner that the empty dishes leave the dispensing carousels (2a) one by one by escaping in succession from the bottoms of adjacent columns, while filled dishes are inserted one by one into the receiving carousel (2b) via the bases of adjacent columns.

4. Apparatus according to claim 3, characterized in that the columns of dishes contained in said carousels (2a, 2b) rest on a horizontal slab (3) overlying said transfer turntable (1), said slab being pierced at each of the said empty dish dispensing, said dish filling and receiving stations by respective openings (30a, 30 b) allowing dishes to pass from the dispensing carousel (2a) to the turntable (1) and from the turntable to the receiving carousel (2b).

5. Apparatus according to claim 4, characterized in that said apparatus includes means for rotating said carousels (2a, 2b), said rotating means importing two successive half-strokes to each carousel for each dish, each half-stroke corresponding to one half of the angular spacing between two adjacent columns.

6. Apparatus according to claim 5, characterized in that two transfer pistons (4a, 4b) are provided, one situated at the dispensing station and the other at the receiving station, the pistons being slightly smaller in diameter than the dishes, and means for displacing the pistons (4a, 4b) vertically on the axes of the associated openings (30a, 30b).

7. Apparatus according to claim 6, characterized in that the said pistons displacing means (42) serve to bring each piston (4a, 4b) into each of the following positions in succession:

(a) a high position in which the top face (48) of the piston lies substantially flush with said horizontal slab (3);

(b) an intermediate position in which the top face (48) lies below the level of the horizontal slab (3) by an amount corresponding substantially to the height of one dish (9); and (c) a low position in which the top face (48) lies substantially flush with said sole plate (55).

8. Apparatus according to claim 6, characterized in that a top face (48) of each piston (4a, 4b) has a sloping flat surface (400) and/or a chamfer (401).

9. Apparatus according to claim 1, characterized in that the transfer turntable (1) is driven by means of horizontal drive disk (6) disposed immediately beneath the sole plate (55) vertically below the turntable (1), said drive disk (6) and the bottom plate (11) each being provided with a series of magnets (61, 12) regularly distributed around their respective peripheries and facing one another.

10. Apparatus according to claim 1, characterized in that the said bottom plate (11) bears against the sole plate (55) via antifriction means, said antifriction means comprising balls (14) and/or ball bearings.

11. Apparatus according to claim 1, characterized in that said filling station comprises a nozzle (70) for injecting a substance including gelose (95), which nozzle is fed by a pump and is normally positioned horizontally between the two plates (10, 11) of the transfer turntable, with the nozzle (70) being carried by a lever (7) capable being retracted by being tilted so as to disengage the access to the sole plate (55), thereby enabling said turntable (1) to be removed.

12. Apparatus according to claim 1, characterized in that said bottom plate (11) is notched to the outside of each of its openings (110), thereby enabling the presence of a dish bottom (90) in each opening to be detected by an opto-electronic detector means (72) situated at the filling station.

13. Apparatus according to claim 1, characterized in that it includes a germicidal device comprising an ultraviolet radiating tube (33) to which the dishes (9) are exposed as they pass to the filling station.

* * * * *